United States Patent [19]

Southgate et al.

[11] Patent Number: 4,820,701
[45] Date of Patent: Apr. 11, 1989

[54] PENAM DERIVATIVES

[75] Inventors: Robert Southgate; Colin H. Frydrych, both of Betchworth, England

[73] Assignee: Beecham Group p.l.c., England

[21] Appl. No.: 112,103

[22] Filed: Oct. 21, 1987

[51] Int. Cl.⁴ .................... C07D 499/76; A61K 31/43
[52] U.S. Cl. .................... 514/194; 514/196; 540/313; 540/314
[58] Field of Search .................... 540/221, 313, 314; 514/201, 196, 194

[56] References Cited

U.S. PATENT DOCUMENTS

| | | | |
|---|---|---|---|
| 4,183,850 | 1/1980 | Darby et al. | 260/239.1 |
| 4,539,149 | 9/1985 | Milner | 260/239.1 |
| 4,609,652 | 9/1986 | Milner | 540/221 |

FOREIGN PATENT DOCUMENTS 0043205  1/1982  European Pat. Off. .

*Primary Examiner*—Nicholas S. Rizzo
*Attorney, Agent, or Firm*—Jacobs & Jacobs

[57] ABSTRACT

Antibacterial agents have the formula (I) or are pharmaceutically acceptable salts or in vivo hydrolysable esters thereof:

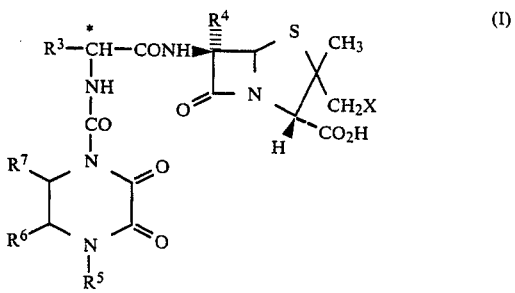

wherein $R^3$ is phenyl, substituted phenyl, cyclohexenyl, cyclohexadienyl or an optionally substituted 5- or 6-membered heterocyclic ring containing up to three hetero atoms selected from oxygen, sulphur or nitrogen, $R^4$ is hydrogen or formamido, $R^5$ is hydrogen, $C_{1-6}$ alkyl, substituted alkyl, aryl or aralkyl, $R^6$ and $R^7$ are the same or different and represent hydrogen, $C_{1-6}$ alkyl, substituted alkyl, halogen, amino, phenyl, substituted phenyl, hydroxyl or $C_{1-6}$ alkoxy or $R^6$ and $R^7$ form the residue of an optionally substituted 5- or 6-membered carbocyclic ring or a 5- or 6-membered heterocyclic ring containing up to three hetero atoms selected from oxygen, sulphr or nitrogen, and X represents

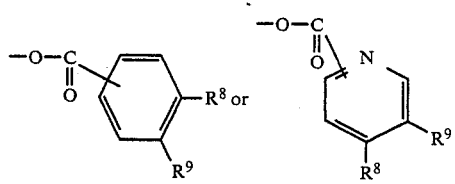

or tautomers thereof wherein $R^8$ and $R^9$ are the same or different and each represents hydroxy, or protected hydroxy.

30 Claims, No Drawings

PENAM DERIVATIVES

This invention relates to a class of novel β-lactam compounds which have antibacterial activity and are of value in the treatment of infections in animals especially mammals, including man, caused by a wide range of micro-organisms, particularly Gram-negative organisms. The invention also relates to a process for the preparation of such compounds, intermediates for use in the preparation of the compounds and to pharmaceutical compositions containing the antibacterially active compounds.

UK Patent GB-2107307B discloses and claims a β-lactam antibiotic having an α-formamido substituent on the carbon atom adjacent to the carbonyl group of the β-lactam ring, and more particularly a compound of formula (A) or a salt thereof:

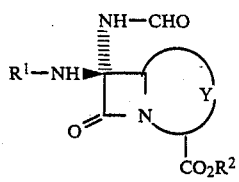

wherein $R^1$ is hydrogen, an acyl group in particular those found on antibacterially active penicillins or cephalosporins, or an amino protecting group; $R^2$ is hydrogen or a readily removable carboxyl protecting group; and Y is

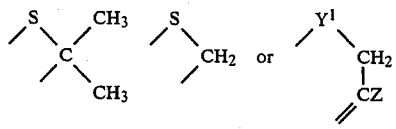

wherein $Y^1$ is oxygen, sulphur or —$CH_2$— and Z represents hydrogen, halogen or an organic group such as $C_{1-4}$ alkoxy, —$CH_2$—Q or —CH=CH—Q where Q represents hydrogen, halogen, hydroxy, mercapto, cyano, carboxy, carboxylic ester, $C_{1-4}$ alkyloxy, acyloxy, aryl, a heterocyclyl group bonded via carbon, a heterocyclylthio group or a nitrogen containing heterocyclic group bonded via nitrogen.

The present invention provides a compound of formula (I) or a pharmaceutically acceptable salt or in vivo hydrolysable ester thereof:

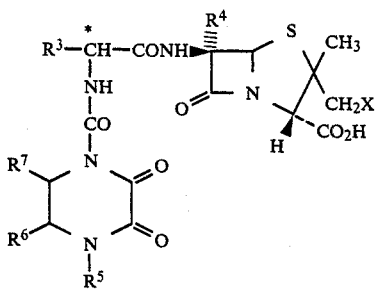

wherein $R^3$ is phenyl, substituted phenyl, cyclohexenyl, cyclohexadienyl or a 5- or 6-membered heterocyclic ring containing up to three hetero atoms selected from oxygen, sulphur or nitrogen optionally substituted with hydroxy, amino, substituted amino, halogen or $C_{1-6}$ alkoxy, $R^4$ is hydrogen or formamido, $R^5$ is hydrogen, $C_{1-6}$ alkyl, substituted alkyl, aryl or aralkyl, $R^6$ and $R^7$ are the same or different and represent hydrogen, $C_{1-6}$ alkyl, substituted alkyl, halogen, amino, phenyl, substituted phenyl, hydroxy or $C_{1-6}$ alkoxy or $R^6$ and $R^7$ form the residue of a 5- or 6-membered carbocyclic ring or a 5- or 6-membered heterocyclic ring containing up to three hetero atoms selected from oxygen, sulphur or nitrogen optionally substituted with hydroxy, amino, substituted amino, halogen or $C_{1-6}$ alkoxy and wherein X represents

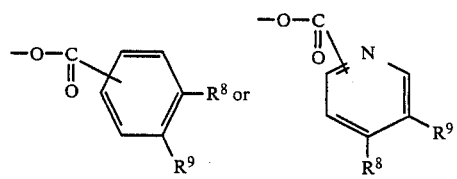

or tautomers thereof wherein $R^8$ and $R^9$ are the same or different and each represents hydroxy, or protected hydroxy.

Suitable protected hydroxy groups include $C_{1-6}$ alkylcarbonyloxy such as acetoxy, $C_{1-6}$ alkoxycarbonyloxy such as t-butoxycarbonyloxy, substituted $C_{1-6}$ alkoxycarbonyloxy wherein the alkyl is substituted by up to three halogen groups, such as trichloroalkoxycarbonyloxy, aralkyloxycarbonyloxy, substitited aralkyloxy carbonyloxy such as p-nitrobenzyloxycarbonyloxy, tri $C_{1-6}$ alkylsilyloxy such as trimethylsilyloxy, or optionally substituted aralkyloxy such as benzyloxy.

When used herein the term 'aryl' includes phenyl and naphthyl optionally substituted with up to five, preferably up to three, groups selected from halogen, $C_{1-6}$ alkyl, phenyl, $C_{1-6}$ alkoxy, halo($C_{1-6}$) alkyl, hydroxy, amino, nitro, carboxy, $C_{1-6}$ alkoxycarbonyl, $C_{1-6}$ alkoxycarbonyl-($C_{1-6}$)-alkyl, $C_{1-6}$ alkylcarbonyloxy, or $C_{1-6}$ alkylcarbonyl groups.

When used herein the term 'alkyl' includes straight and branched chain alkyl groups containing from 1 to 6 carbon atoms, such as methyl, ethyl, propyl and butyl. A particular alkyl group is methyl.

The term 'halogen' refers to fluorine, chlorine, bromine and iodine.

Suitably the substituted phenyl group for $R^3$, $R^6$ or $R^7$ is a phenyl group substituted with up to three groups selected from $C_{1-6}$ alkyl, phenyl, halogen, $C_{1-6}$ alkoxy, amino, nitro, hydroxy, $C_{1-6}$ alkylamido, $C_{1-6}$ alkylcarbonyloxy, carboxy, $C_{1-6}$ alkoxycarbonyl, halo($C_{1-6}$)alkyl, oxo($C_{1-6}$)alkyl, $C_{1-6}$ alkylcarbonyl, aryloxy, aralkyloxy, arylcarbonyl, $C_{1-6}$ alkylamino or di($C_{1-6}$)alkylamino or protected amino. Suitable amino protecting groups are those well known in the art which may be removed under conventional conditions without disruption of the remainder of the molecule.

Suitable amino-protecting groups include benzyl optionally substituted in the phenyl ring by one or two substituents selected from $C_{1-4}$ alkyl, $C_{1-4}$ alkoxy, trifluoromethyl, halogen or nitro; $C_{1-4}$ alkoxycarbonyl, for example tert-butoxycarbonyl; halogen substituted $C_{1-4}$ alkoxycarbonyl for example trichloroethoxycarbonyl; benzyloxycarbonyl optionally substituted as for benzyl above; allyloxycarbonyl; trityl; or enamines derived from reaction with β ketocarboxylic acid esters, for example from ethylacetoacetate.

In formula (I) the group $R^3$ is preferably phenyl or 4-hydroxyphenyl.

Suitable $C_{1-6}$ alkyl groups for the groups $R^5$, $R^6$ and $R^7$ include methyl, ethyl n- and iso-propyl and n-, sec-, iso- and tert-butyl. Preferably $R^5$ is ethyl and $R^6$ and $R^7$ are hydrogen.

Preferbly $R^8$ and $R^9$ are the same and each represents hydroxy or acetoxy.

Preferred compounds of formula (I) have a methyl substituent in the 2α-position of the penam nucleus and a substituted methyl substituent in the 2α-position.

The carbon atom marked * in formulae herein is asymmetric and thus compounds of formula (I) may exist as two optically active diastereoisomers. In general the isomer prepared from the D-side chain exhibits the highest antibacterial activity and accordingly the D compound or the DL mixtures are preferred, with the D compound being particularly preferred.

The compounds of formula (I) with the preferred D-side chain can be separated from a mixture of both diastereoisomers by conventional methods, or be prepared from intermediates that bear a D-side chain.

Moreover where $R^4$ represents the formamido group, this can exist in two preferred conformations, those wherein the hydrogen atoms of the —NH—CHO are, cis- or trans-, of which the cis conformation normally predominates.

Since the β-lactam antibiotic compounds of the present invention are intended for use in pharmaceutical compositions it will readily be understood that they are each provided in substantially pure form, for example at least 50% pure, more suitably at least 75% pure and preferably at least 95% pure (% are on a wt/wt basis). Impure preparations of the compounds may be used for preparing the more pure forms used in the pharmaceutical compositions. Although the purity of intermediate compounds of the present invention is less critical it will readily be understood that the substantially pure form is preferred as for the β-lactam antibiotic compounds. Preferably, whenever possible, the compounds of the present invention are obtained in crystalline form.

Examples of suitable pharmaceutically acceptable in vivo hydrolysable ester groups include those which break down readily in the human body to leave the parent acid or its salt. Suitable ester groups of this type include those of part formula (i), (ii), (iii) and (iv):

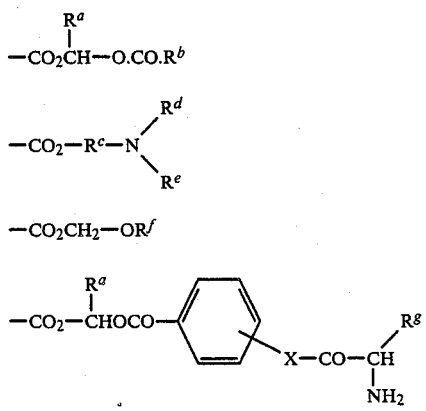

wherein $R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{1-6}$ alkyl $C_{3-7}$ cycloalkyl, 1-amino $C_{1-6}$ alkyl, or 1-($C_{1-6}$ alkyl)amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group and $R^d$ and $R^e$ independently represent $C_{1-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; and X is oxygen or NH.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

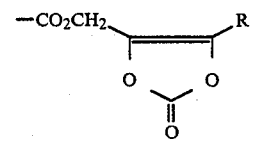

wherein R is hydrogen, $C_{1-6}$ alkyl or phenyl.

Suitable pharmaceutically acceptable salts of the carboxy group of the compound of formula (I) include metal salts, eg aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)amine, cycloalkylamines such as dicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins. Other useful salts include the lithium and silver salt.

Some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

Specific compounds within this invention include the following and pharmaceutically acceptable salts and in vivo hydrolysable esters thereof:

2β-(3,4-Diacetoxybenzoyloxy)methyl-6β-[R,2-(4-ethyl-2,3-dioxopiperazin-1-yl)carbonylamino-2-phenylacetamido]-6α-formamido-2α-methylpenam-3-carboxylic acid;

6β-[R,2-(4-Ethyl-2,3-dioxopiperazin-1-yl)carbonylamino-2-phenylacetamido]-6α-formamido-2β-

(3,4-dihydroxybenzoyloxy)methyl-2α-methylpenam-3-carboxylic acid;

2β-(3,4-Diacetoxybenzoyloxy)methyl-6β-[R,2-(4-ethyl-2,3-dioxopiperazin-1-yl)carbonylamino-2-phenylacetamido]-2α-methylpenam-3-carboxylic acid; and 6β-[R,2-(4-Ethyl-2,3-dioxopiperazin-1-yl)carbonylamino-2-phenylacetamido]-2β-(3,4-dihydroxybenzoyloxy)methyl-2α-methylpenam-3-carboxylic acid.

The antibiotic compounds according to the invention may be formulated for administration in any convenient way for use in human or veterinary medicine, according to techniques and procedures per se known in the art with reference to other antibiotics, and the invention therefore includes within its scope a pharmaceutical composition comprising an antibiotic compound according to the present invention such as, for example a compound of formula (I) above together with a pharmaceutically acceptable carrier or excipient.

The compositions may be formulated for administration by any suitable route, such as oral or parenteral, or by topical application. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparation may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository base, eg cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compound may contain from 0.1% to 99.5% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 mg to 12 g per day for an average adult patient (70 kg), for instance 1500 mg per day depending on the route and frequency of administration. Such dosages correspond to 1.5 to 170 mg/kg per day. Suitably the dosage is from 1 g to 6 g per day. The daily dosage is normally given by administering the compound 1 to 4 times daily.

The antibiotic compounds according to the present invention may be the sole therapeutic agent in the compositions of the invention or a combination with other antibiotics and/or β-lactamase inhibitor may be employed.

Advantageously the compositions also comprise a compound of formula (B) or a pharmaceutically acceptable salt or ester thereof:

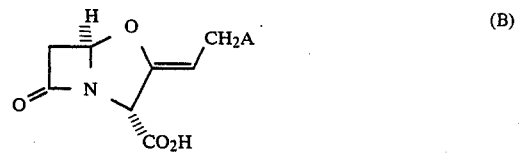

(B)

wherein A is hydroxyl; substituted hydroxyl; thiol; a group of formula $SO_2R^j$ wherein $R^j$ is $C_{1-6}$ alkyl; substituted thiol; amino; mono- or di-hydrocarbyl substituted amino; mono- or di-acylamino; an optionally substituted triazolyl group; or an optionally substituted tetrazolyl group as described in EP No. O 053 893.

A further advantageous composition comprises an antibiotic compound according to the invention and a pharmaceutically acceptable carrier or excipient together with a β-lactamase inhibitor of formula (C) or a pharmaceutically acceptable salt or in vivo hydrolysable ester thereof:

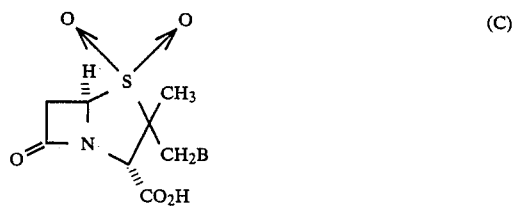

(C)

wherein B is hydrogen, halogen or a group of formula:

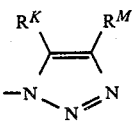

in which $R^K$ and $R^M$ are the same or different and each is hydrogen, $C_{1-6}$ alkoxycarbonyl, or carboxy or a pharmaceutically acceptable salt thereof.

Further suitable β-lactamase inhibitors include 6-alkylidine penems as described in European patent application No. 81301683.9 (Publication No. 0 041 768.

Further suitable β-lactamase inhibitors include 6β-bromopenicillanic acid and salts and in vivo hydrolysable esters thereof and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of an antibiotic compound of this invention.

The antibiotic compounds of the present invention are active against a broad range of Gram positive and Gram negative bacteria, for example they are useful for treatment of respiratory tract and urinary tract infections in humans and are particularly useful in the treatment of bacterial infections in immunocompromised patients. A particular advantage of the antibacterially active compounds of the invention in which $R^4$ is formamido, is their stability to β-lactamase enzymes and they are therefore effective against β-lactamase producing organisms.

The present invention further provides a process for the preparation of a compound of formula (I) or a pharmaceutically acceptable salt or pharmaceutically acceptable in vivo hydrolysable ester thereof, which process comprises treating a compound of formula (II):

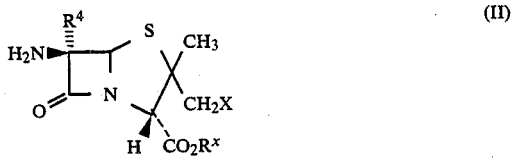
(II)

or a compound of formula (II) wherein the amino group is substituted by a group which permits acylation, wherein $R^4$ and X are as defined in respect of formula (I) and $R^x$ represents hydrogen or a readily removable carboxyl protecting group with an N-acylating derivative of an acid of formula (III)

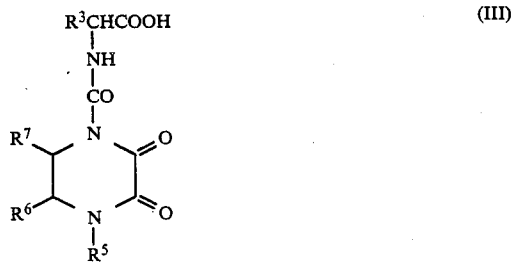
(III)

wherein $R^3$, $R^5$, $R^6$ and $R^7$ are as defined in respect of formula (I) and wherein any reactive groups therein may be protected and thereafter if necessary carrying out one or more of the following steps:

(i) removing any carboxyl protecting groups $R^x$;
(ii) removing any protecting groups on $R^3$;
(iii) removing any protecting group on X;
(iv) converting the product into a pharmaceutically acceptable salt or in vivo hydrolysable ester.

Suitable readily removable carboxyl protecting groups for the group $R^x$ include salt and ester derivatives of the carboxylic acid. The derivative is preferably one which may readily be cleaved.

Suitable ester-forming carboxyl-protecting groups are those which may be removed under conventional conditions. Such groups for $R^x$ include benzyl, p-methoxybenzyl, benzoylmethyl, p-nitrobenzyl, 4-pyridylmethyl, t-butyl, t-amyl, allyl, diphenylmethyl, triphenylmethyl, adamantyl, 2-benzyloxyphenyl, 4-methylthiophenyl, tetrahydrofuran-2-yl, tetrahydropyran-2-yl, pentachlorophenyl, acetonyl, toluenesulphonylethyl, methoxymethyl, a silyl, stannyl or phosphorus-containing group or an in vivo hydrolysable ester radical such as defined above.

A carboxyl group may be regenerated from any of the above esters by usual methods appropriate to the particular $R^x$ group, for example, acid- and base-catalysed hydrolysis, or by enzymically-catalysed hydrolysis, or by hydrogenolysis.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula $-P.R^p R^q$ wherein $R^p$ is an alkyl, haloalkyl, aryl, aralkyl, alkoxy, haloalkyl, aryl, aralkyl, alkoxy, haloalkoxy, aryloxy, aralkyloxy or dialkylamino group, $R^q$ is the same as $R^p$ or is halogen or $R^p$ and $R^q$ together form a ring; suitable such phosphorus groups being $-P(OC_2H_5)_2$, $-P(C_2H_5)_2$,

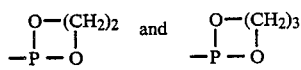

An appropriate reactive N-acylating derivative of the acid (III) is employed in the above process.

Suitable N-acylating derivatives include an acid halide, preferably the acid chloride or bromide. Acylation with an acid halide may be effected in the presence of an acid binding agent for example, tertiary amine (such as pyridine or dimethylaniline), an inorganic base (such as calcium carbonate or sodium bicarbonate) or an oxirane, which binds hydrogen halide laberated in the acylation reaction. The oxirane is preferably a ($C_{1-6}$)—1,2-alkylene oxide—such as ethylene oxide or propylene oxide. The acylation reaction using an acid halide may be carried out at a temperature in the range $-50°$ C. to $+50°$ C., preferably $-20°$ C. to $+20°$ C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (III) or a salt or suitable derivative thereof with a halogenating (eg chlorinating or brominating) agent such as phosphorus pentachloride, thionyl chloride or oxalyl chloride.

Alternatively, the N-acylating derivative of the acid (III) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric or phosphorous acids) or aliphatic or aromatic sulphonic acids (such as p-toluenesulphonic acid). When a symmetrical anhydride is employed, the reaction may be carried out in the presence of 2,6-lutidine as catalyst.

Alternative N-acylating derivatives of acid (III) are the acid azide, or activated esters such as esters with 2-mercaptopyridine, cyanomethanol, p-nitrophenol, 2,4-dinitrophenol, triophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, di-n-propyl- or diisopropylcarbodiimide, N,N'-di-cyclohexylcarbodiimide, or N-ethyl-N'-[3-(dimethylamino)propyl]carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$—$C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

The compounds of formula (I) may also suitably be prepared by reacting a compound of formula (IV):

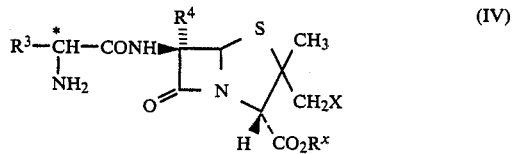

(IV)

wherein $R^3$, $R^4$, X, $R^x$ and * are as hereinbefore defined and the α-amino group is optionally substituted with a group which permits acylation to take place, and any reactive groups may be protected; with an N-acylating derivative of an acid of formula (V):

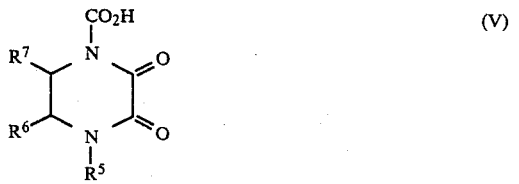

(V)

wherein $R^5$, $R^6$ and $R^7$ are as defined with respect to formula (I) and any reactive groups may be protected and thereafter, if necessary, carrying out one or more of the following steps:

(i) removing any carboxyl protecting group $R^x$;
(ii) removing any protecting groups on $R^3$;
(iii) removing any protecting group on X;
(iv) converting the product into a salt or in vivo hydrolysable ester.

The compounds of formula (IV) herein which are inter alia intermediates for the compounds of formula (I) as hereinbefore defined may be prepared by reacting a compound of formula (II) with an N-acylating derivative of an acid of formula (VI):

(VI)

wherein $R^3$ and * are as hereinbefore defined and $R^{10}$ is an amino protecting group; and thereafter removing the protecting group $R^{10}$.

Suitable amino-protecting groups $R^{10}$ include those disclosed hereinabove in respect of $R^3$, $R^6$ and $R^7$. Particularly preferred groups $R^{10}$ are 4-nitrobenzyloxycarbonyl and trichloroethyloxycarbonyl.

Compounds of formula (IV) may also be prepared by reacting a compound of formula (II) with an N-acylating derivative of an α-azido acid of formula:

(VII)

wherein $R^3$ and * are as hereinbefore defined; followed by reduction of the azido group to an amino group by conventional methods such as catalytic hydrogenation or dissolving metal reduction.

The intermediate compound of formula (II) or a salt thereof as hereinbefore defined may suitably be prepared by reacting a compound of formula (VIII):

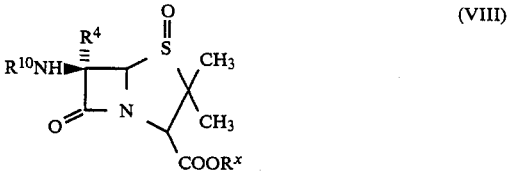

(VIII)

wherein $R^4$, $R^{10}$ and $R^x$ are as hereinbefore defined with a thiol compound $R^{11}SH$ or a salt thereof, where $R^{11}$ is a thiol residue, to give a compound of formula (IX):

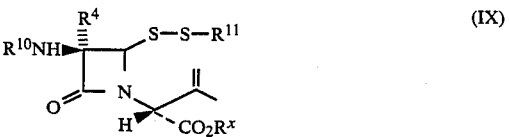

(IX)

wherein $R^{11}$, $R^4$, $R^{10}$ and $R^x$ are as hereinbefore defined and thereafter reacting the compound of formula (IX) with a salt of an acid of formula (X):

XH                                              (X)

wherein X is as defined in respect of formula (I) and thereafter if necessary carrying out one or more of the following steps:

(i) removing any amino protecting group $R^{10}$;
(ii) removing any protecting group on X;
(iii) converting the product into a salt.

Suitable thiol compounds for use in this process include substitutes or unsubstituted aliphatic thiols, aromatic thiols and heterocyclic thiols. Suitable thiols are disclosed in U.S. Pat. No. 3,954,732. Preferred thiols are fused aryl/heterocyclic thiols such as 2-mercaptobenzothiazole.

The salt of the acid of formula (X) may be an alkali metal salt, an alkaline earth metal salt, or a heavy metal salt. A particularly useful salt is the silver salt. The reaction is normally carried out in the presence of iodine.

Compounds of formula (VIII) may be prepared by the oxidation of a corresponding compound of formula (XI):

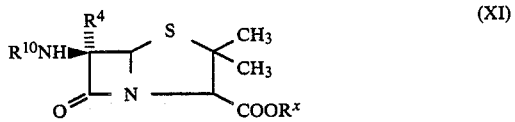

wherein $R^4$, $R^{10}$ and $R^x$ are as hereinbefore defined.

Such oxidation may conveniently be performed in conventional manner, for example using a per-acid such as peracetic acid or m-chloro-perbenzoic acid, suitably at an ambient or depressed temperature. Suitable solvents for such oxidation include ethyl acetate, chloroform, dichloromethane, dioxan and tetrahydrofuran.

Processes for the preparation of compounds of formula (XI) in which $R^4$ is formamido are disclosed or are analogous to those disclosed in U.K. Patent GB No. 2107307B. Processes for the preparation of compounds of formula (VIII) in which $R^4$ is formamido are disclosed in European Patent Application No. 84300339.3 (Publication No. 0114752).

The present invention further provides a process for the preparation of a compound of formula (I) wherein $R^4$ is formamido by reacting a compound of formula (XII):

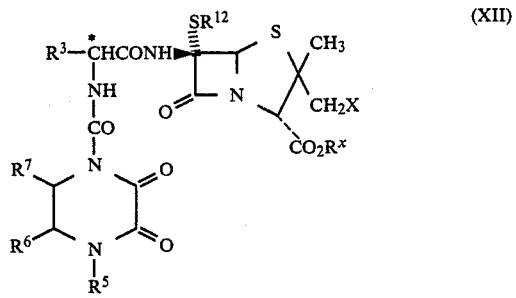

wherein $R^3$, $R^5$, $R^6$, $R^7$, X, $R^x$ and * are as hereinbefore defined, $R^{12}$ is $C_{1-6}$ alkyl, aryl or benzyl; and wherein any reactive groups may be protected; with a heavy metal ion such as mercury, silver, thallium, lead or copper and thereafter in situ with a nucleophilic derivative of formamide. This process is analogous to processes disclosed in European Patent Application No. 84300338.5 (Publication No. 0115405).

Compounds of formula (XII) may be prepared from a compound of formula (I) in which $R^4$ is hydrogen by processes such as those disclosed in UK Patent GB-2107307B.

Compounds of formula (I) wherein $R^4$ is formamido may also be prepared by formylating a compound of formula (XIII):

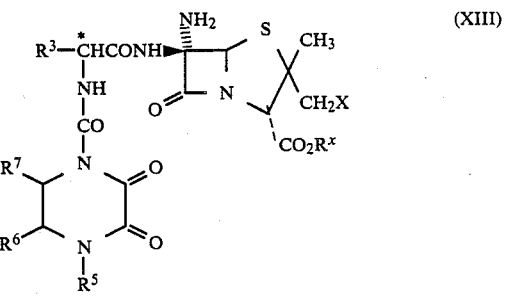

wherein $R^3$, $R^5$, $R^6$, $R^7$, $R^x$, X and * are as hereinbefore defined and wherein any reactive groups may be protected. This process is analogous to processes disclosed in U.K. Patent No. 2107307B.

Compounds of formula (XIII) may be prepared from a compound of formula (I) in which $R^4$ is hydrogen by processes such as those disclosed in U.K. Patent GB-2107307B.

It will be appreciated that compounds of formula (II) are novel and useful intermediates which, accordingly, form another aspect of the present invention. Specific compounds within formula (II) include:

Benzyl 6β-amino-2β-(3,4-diacetoxybenzoyloxy)-methyl-6α-formamido-2α-methylpenam-3-carboxylate;

Benzyl 6β-amino-2β-(3,4-diacetoxybenzoyloxy)-methyl-2α-methylpenan-3-carboxylate.

The antibiotic compounds of the invention are active against a wide range of Gram-negative and Gram positive organisms including *E. coli* such as NCTC 10418, JT 425 DC 2 and DCO, *Pseudomonas* Spp. such as *Ps. aeruginosa* for example 10662 and K79961, and *Klebsiella pneumoniae* T 767. Compounds of formula (I) in which $R^4$ is formamido exhibit improved β-lactamase stability over those in which $R^4$ is hydrogen.

The following Examples illustrate the preparation and biological activity of the compounds of the present invention.

PREPARATION NO. 1

Benzyl 6β-trichloroethoxycarbonylamino-6α-formamidopenicillanate-1-oxide

A solution of benzyl 6β-trichloroethoxycarbonylamino-6α-formamidopenicillanate (10 g, 19.06 mmol) in dry $CH_2Cl_2$ (100 ml) was treated with 85% mCPBA (5.8 g, 28.6 mmol). The resulting suspension was stirred for 30 minutes then washed with saturated aqueous $NaHCO_3$, 10% aqueous $NaHSO_3$, again with saturated aqueous $NaHCO_3$ and finally with brine. Drying over $MgSO_4$ and evaporation under reduced pressure provided the title compound (8.8 g); the pure α- and β-isomers may be obtained by column chromatography on silica gel, eluting with mixtures of ethyl acetate and hexane.

Isomer 1

$v_{max}$ (KBr) 1797, 1742, 1694 and 1047 cm$^{-1}$; $\delta_H$ (CDCl$_3$) 8.53 (d, 11.5 Hz) and 8.20 (d, 0.7 Hz), (Total 1H), 8.07 (1H, s), 7.34 (1H, s), 7.38 (5H, s), 5.22 (2H, ABq), 5.17 (1H, s), 4.97–4.70 (2H, m), 4.58 (1H, s), 1.80 and 1.27 (6H, 2s); [F.A.B. (3-Nitrobenzylalcohol) (+ve ion) MH+540].

Isomer 2

$\nu_{max}$ (KBr) 1796, 1733, 1695 and 1061 cm$^{-1}$; $\delta_H$ (CDCl$_3$) 8.51 (d, 11.4 Hz) and 8.26 (d, 0.7 Hz) (Total 1H), 7.46 (1H, m), 6.79 (1H, s), 7.39 (5H, s), 5.26 (2H, ABq), 5.19 (1H, s), 4.76 (1H, m), 4.73 (2H, m), 1.63 and 1.09 (6H, 2s); [F.A.B. (3-Nitrobenzylalcohol) (+ve ion) MH+540].

PREPARATION NO. 2

Benzyl 4-(benzothiazole-2-yl)dithio-3β-trichloroethoxycarbonylamino-3α-formamido-α-isopropenyl-2-oxoazetidine-1-acetate A mixture of benzyl 6β-trichloroethoxycarbonylamino-6α-formamidopenicillanate-1-oxides (679 mg, 1.26 mmol) and 2-mercaptobenzothiazole (231 mg, 1.38 mmol) was dissolved in dry benzene (20 ml) and the solution heated to reflux for 3½ hours. The solvent was then removed under reduced pressure and the residue chromatographed on silica gel. Elution with ethyl acetate/hexane mixtures gave the title compound (504 mg) as an off-white amorphous solid; $\nu_{max}$ (CH$_2$Cl$_2$) 3380, 3250, 1790, 1740 and 1695 cm$^{-1}$; $\delta_H$ (CDCl$_3$) 8.63 (d, 12 Hz) and 8.00 (s) (Total 1H), 7.97 (d, 7.1 Hz), 7.34 (9H, m), 5.55 (1H, s), 5.19 (2H, ABq), 5.15 (2H, s), 5.01 (1H, d, 5.1 Hz), 5.05-4.65 (2H, m), 1.92 (3H, s); [F.A.B. (3-Nitrobenzylalcohol/sodium) (+ve ion) MNa+711].

PREPARATION NO. 3

Benzyl 2β-(3,4-diacetoxybenzoyloxy)methyl-6β-trichloroethoxycarbonylamino-6α-formamido-2α-methylpenam-3-carboxylate Silver 3,4-diacetoxybenzoate (1.598 g, 4.64 mmol) was suspended in dry benzene (20 ml) and iodine (588 mg, 2.32 mmol) was added. The resulting slurry was stirred vigorously for 1 hour. Benzyl 4-(benzothiazole-2-yl)dithio-3β-trichloroethoxycarbonylamino-3α-formamido-α-isopropenyl-2-oxoazetidine-1-acetate (800 mg, 1.16 mmol) in dry CH$_2$Cl$_2$ (22 ml) was added and stirring continued at ambient temperature for 18 hours. The mixture was then filtered through a plug of Kieselguhr and the filtrate diluted with EtOAC. The solution was then washed with water, saturated aqueous NaHCO$_3$ and brine, then dried with MgSO$_4$. Evaporation under reduced pressure gave a residue which was chromatographed on silica gel. Elution with mixtures of ethyl acetate and hexane gave the title compound (168 mg) as an amorphous white solid; $\nu_{max}$ (CH$_2$Cl$_2$) 3380, 3300, 1795, 1780, 1740, 1705 and 1605 cm$^{-1}$; $\delta_H$ (CDCl$_3$) 8.50 (d, 11.7 Hz) and 8.22 (d, 0.7 Hz) (Total 1H), 7.92 (1H, dd, 8.5 and 2.1 Hz), 7.87 (1H, d, 2.0 Hz), 7.39 (5H, m), 7.28 (1H, d, 8.5 Hz), 7.14-6.70 (1H, m), 5.70 (s) and 5.60 (s) (Total 1H), 5.24 (2H, m), 4.94 (s) and 4.92 (s) (Total 1H), 4.71 (2H, m), 4.39 (1H, d, 11.9 Hz), 4.12 (1H, d, 11.9 Hz), 1.45 (s) and 1.43 (Total 3H).

PREPARATION NO. 4

Benzyl 6β-amino-2β-(3,4-diacetoxybenzoyloxy)methyl-6α-formamido-2α-methylpenam-3-carboxylate Benzyl 2β-(3,4-diacetoxybenzoyloxy)methyl-6β-trichloroethoxycarbonylamino-6α-formamido-2α-methylpenam-3-carboxylate (168 mg, 0.22 mmol) was dissolved in dry THF (28 ml) and 1M aqueous KH$_2$PO$_4$ (8.4 ml) was added. Freshly activated zinc powder (1.0 g) was added and the pH adjusted to 4 with 2.5M aqueous HCl. The pH was maintained at 4 as necessary with further additions of acid. The reaction was monitored by TLC; after 3 h the mixture was filtered through a Kieselguhr plug and the filtrate evaporated under reduced pressure. The residue was partitioned between EtOAc and water; the organic phase was separated and washed with saturated aqueous NaHCO$_3$ and brine. After drying with MgSO$_4$ and evaporation of the solvent under reduced pressure the residue was chromatographed on silica gel. Elution with mixtures of ethyl acetate and hexane, followed by concentration of the product-containing eluant gave the title compound (76 mg) as an amorphous white solid; $\nu_{max}$ (CH$_2$Cl$_2$) 3400, 3310, 1780, 1745, 1725 and 1695 cm$^{-1}$; $\delta_H$(CDCl$_3$) 8.41 (d, 11.8 Hz) and 8.22 (d, 1.1 Hz) (Total 1H), 7.92 (1H, dd, 8.5 and 2.1 Hz), 7.86 (1H, d, 2.1 Hz), 7.37 (5H, m), 7.28 (1H, d, 8.5 Hz), 6.27 (1H, s (br)), 5.60 (s) and 5.39 (s) (Total 1H), 5.24 (2H, s), 4.87 (s) and 4.86 (s) (Total 1H), 4.44 (1H, d, 11.5 Hz), 4.16 (1H, d, 11.5 Hz), 2.51 (s) and 2.48 (s, br) (Total 2H), 2.32 and 2.31 (6H, 2s), 1.47 (s) and 1.44 (s) (Total 3H); [F.A.B. (Thioglycerol) (+ve ion) MH+586].

PREPARATION NO. 5(a)

R,2-[(4-Ethyl-2,3-dioxopiperazin-1-yl)carbonylamino]-2-phenylacetyl chloride

To R,2-[(4-ethyl-2,3-dioxopiperazin-1-yl)carbonylamino]-2-phenylacetic acid (124 mg, 0.389 mmol) in dry CH$_2$Cl$_2$ (10 ml), containing a catalytic quantity of dry DMF, was added oxalyl chloride (99 mg, 0.78 mmol). The mixture was stirred for 1½ hours, then evaporated at reduced pressure. The residue was taken up in dry CH$_2$Cl$_2$ and re-evaporated (×2). The residue was dried in vacuo and used without further purification; $\nu_{max}$ (CH$_2$Cl$_2$) 3280, 1800, 1720 and 1695 cm$^{-1}$.

PREPARATION NO. 5(b)

Benzyl 2β-(3,4-diacetoxybenzoyloxy)methyl-6β-[R,2-(4-ethyl-2,3-dioxopiperazin-1-yl)carbonylamino-2-phenylacetamido]-6α-formamido-2α-methylpenam-3-carboxylate Benzyl 6β-amino-3β-(3,4-diacetoxybenzoyloxy)-methyl-6α-formamido-2α-methylpenam-3-carboxylate (76 mg, 0.13 mmol) was dissolved in dry CH$_2$Cl$_2$ (6 ml) and R,2-[(4-ethyl-2,3-dioxopiperazin-1-yl)carbonylamino]-2-phenylacetyl chloride (0.39 mmol) was added as a solution in dry CH$_2$Cl$_2$ (4 ml). Pyridine (31 mg, 0.39 mmol) and dimethylaminopyridine (16 mg, 0.13 mmol) were added; the mixture was then stirred for 22 hours. Fresh CH$_2$Cl$_2$ was then added and the organic solution washed with 0.1M aqueous HCl, saturated aqueous NaHCO$_3$ and brine. After drying with MgSO$_4$ and evaporation of the solvent under reduced pressure the residue was chromatographed on silica gel. Elution with mixtures of methanol and ethyl acetate provided the title compound (89 mg) as a white solid; $\nu_{max}$ (CH$_2$Cl$_2$) 3280, 1785, 1745, 1720 and 1690 cm$^{-1}$; $\delta_H$ (CD$_3$COCD$_3$) (Major rotamer) 10.16 (1H, d, 6.9 Hz), 9.04 (1H, s), 8.31 (1H, s), 8.45 (d, 12 Hz) and 8.19 (d, 1.0 Hz) (Total 1H), 7.92 (1H, dd, 8.4 and 2.0 Hz), 7.88 (1H, d, 1.8 Hz), 7.61-7.29 (11H, m), 5.75 (1H, d, 6.8 Hz), 5.64 (1H, s), 5.25 (2H, s), 4.91 (1H, s), 4.07-4.01 (m) and 3.71-3.63 (m) and 3.58-3.46 (m) (Total 8H), 2.33 (3H, s), 2.32 (3H, s), 1.29-1.12 (6H, m); [F.A.B. (Thioglycerol) (+ve ion) MH+887].

EXAMPLE NO. 1

Sodium 2β-(3,4-diacetoxybenzyloxy)methyl-6β-[R,2-(4-ethyl-2,3-dioxopiperazin-1-yl)carbonylamino-2-phenylacetamido[-6α-formamido-2α-methylpenam-3-carboxylate Benzyl 2β-(3,4-diacetoxybenzoyloxy)methyl-6β-[R,2-(4-ethyl-2,3-dioxopiperazin-1-yl)carbonylamino-2-phenylacetamido]-6α-formamido-2α-methylpenan-3-carboxylate (84 mg, 0.095 mmol) was dissolved in dry THF (12 ml) and the solution added to the 10% Pd-charcoal catalyst (89 mg). The mixture was hydrogenated at ambient temperature and pressure for 3 hours. After filtration through a Kieselguhr plug the filtrate was evaporated under reduced pressure. The residue was suspended in distilled water (10 ml) and the pH carefully adjusted to 6.8 using dilute aqueous $NaHCO_3$. The solution was filtered and the filtrate lyophilised to give the title compound (62 mg); $\nu_{max}$(KBr) 1773, 1712, 1680 and 1613 cm$^{-1}$; $\delta_H$ ($D_2O$) 8.42 (s) and 8.10 (s) (Total 1H), 7.96 (1H, dd, 8.7 and 2.1 Hz), 7.87 (1H, d, 1.9 Hz), 7.46–7.26 (6H, m), 5.63 (1H, s), 5.42 (1H, s), 4.53 (1H, s), 3.93 (2H, m), 3.75–3.32 (6H, m), 2.36 (3H, s), 2.35 (3H, s), 1.38 (3H, s), 1.15 (3H, t, 7.3 Hz).

EXAMPLE NO. 2

Sodium 6β-[R,2-(4-ethyl-2,3-dioxopiperazin-1-yl)carbonylamino-2-phenylacetamido]-6α-formamido-2β-(3,4-dihydroxybenzoyloxy)methyl-2α-methylpenam-3-carboxylate A solution of sodium 2β-(3,4-diacetoxybenzoyloxy)methyl-6β-[R,2-(4-ethyl-2,3-dioxopiperazin-1-yl)carbonylamino-2-phenylacetamido]-6α-formamido-2α-methylpenan-3-carboxylate (30 mg, 0.0366 mmol) in 0.05M aqueous $KH_2PO_4$ (10 ml) was treated with a citrus acetyl esterase preparation (ex. Sigma) (0.4 ml, equivalent to approx. 1.6 mg protein). The pH was adjusted to 7.0 with 0.05M aqueous NaOH. The reaction was monitored by reverse phase HPLC. After 1 hour the reaction mixture was chromatographed on HP20SS resin, eluting first with water, then with acetone/water mixtures. The product containing eluant was concentrated under reduced pressure, then lyopholised to give the title compound (17 mg); $\nu_{max}$ (KBr) 1776, 1709, 1677 and 1608 cm$^{-1}$; $\delta_H$ ($D_2O$) 8.40 (s) and 8.08 (s) (Total 1H), 7.50–7.25 (7H, m), 6.93 (1H, d, 8.4 Hz), 5.61 (1H, s), 5.38 (1H, s), 4.54 (1H, s), 3.93 (2H, m), 3.73–3.34 (6H, m), 1.37 (3H, s), 1.15 (3H, t, 7.2 Hz); [F.A.B. (Thioglycerol) (+ve ion) MH+735].

PREPARATION 6

Benzyl 4-(benzothiazole-2-yl)dithio-3β-trichloroethoxycarbonylamino-α-isopropenyl-2-oxoazetidine-1-acetate Benzyl 6β-trichloroethoxycarbonylaminopenicillanate-1-oxide (18 g, 36.2 mmol) was dissolved in dry toluene (450 ml) and 2-mercaptobenzothiazole (6.05 g, 36.2 mmol) was added. The solution was heated to reflux for 1 hour after which time the solvent was removed under reduced pressure. The residue was chromatographed on silica gel, elution with mixtures of ethyl acetate/hexane provided the title compound (8.55 g) as an off-white amorphous solid; $\nu_{max}$ (KBr) 3317, 1779, 1735 cm$^{-1}$; $\delta_H$ (CDCl$_3$) 7.96 (1H, m), 7.79 (1H, m), 7.49–7.24 (7H, m), 6.76 (1H, d, 8.9 Hz), 5.57 (1H, d, 4.7 Hz), 5.41 (1H, dd, 8.9 and 4.7 Hz), 5.21 (1H, d, 1.4 Hz), 5.06 (1H, s), 4.97 (1H, s), 5.18 (2H, ABq), 4.83 (1H, d, 12.0 Hz), 4.68 (1H, d, 12.0 Hz), 1.93 (3H, s).

PREPARATION 7

Benzyl 2β-(3,4-diacetoxybenzoyloxy)methyl-6β-trichloroethoxycarbonylamino-2α-methylpenam-3-carboxylate Silver 3,4-diacetoxybenzoate (2.07 g, 6.0 mmol) was suspended in dry benzene (30 ml) and iodine (774 mg, 3.0 mmol) was added. The resulting slurry was stirred for 1 hour. Benzyl 4-(benzothiazole-2-yl)dithio-3β-trichloroethoxycarbonylamino-α-isopropenyl-2-oxoazetidine-1-acetate (972 mg, 1.5 mmol) in dry $CH_2Cl_2$ (30 ml) was added and the stirring continued for 4 hours. The mixture was then filtered through a plug of Kieselguhr and the filtrate diluted with EtOAc. The solution was then washed with saturated aqueous $NaHCO_3$ and brine then dried over $MgSO_4$. Evaporation of the solvent under reduced pressure gave a residue which was chromatographed on silica gel. Elution with mixtures of ethyl acetate and hexane gave the title compound (422 mg), containing an equimolar quantity of the isomeric cepham, as a white amorphous solid; $\nu_{max}$ ($CH_2Cl_2$) 3400, 3320, 1780 and 1745 cm$^{-1}$; $\delta_H$ (CDCl$_3$) 7.99–7.90 (m) and 7.38–7.26 (m) (Total 8H), 6.63 (d, 9.9 Hz) and 6.06 (d, 8.4 Hz) (Total 1H), 5.63 (d, 4.1 Hz) and 5.53 (dd, 9.9 and 4.1 Hz) and 5.42–5.34 (m) (Total 2H), 5.2 (2H, m), 4.87 (s) and 4.81–4.65 (m) and 4.03 (d, 11.5 Hz) and 3.72 (d, 14.8 Hz) and 3.45 (d, 14.8 Hz) (Total 5H), 2.32 (6H, s), 1.60 (s) and 1.59 (s) (Total 3H); [F.A.B. (3-Nitrobenzylalcohol/sodium) (+ve ion) MNa+739].

PREPARATION 8

Benzyl 6β-amino-2β-(3,4-diacetoxybenzoyloxy)methyl-2α-methylpenam-3-carboxylate

Benzyl 2β-(3,4-diacetoxybenzoyloxy)methyl-6β-trichloroethoxycarbonylamino-2α-methylpenam-3-carboxylate (422 mg, the product from Preparation 8 containing an equimolar quantity of the isomeric cepham) was dissolved in dry THF (20 ml) and 1M aqueous $KH_2PO_4$ (6 ml) was added. Freshly activated zinc powder (1.0 g) was added and the mixture stirred rapidly; the pH was adjusted to 4 with 2.5M aqueous HCl. Further additions of zinc were made to complete the reaction, with the pH maintained at 4 with 2.5M aqueous HCl. After 1½ hours the reaction mixture was filtered through a plug of Kieselguhr and the filtrate concentrated under reduced pressure. The residue was partitioned between EtOAc and saturated aqueous $NaHCO_3$; the organic phase was separated and washed with saturated aqueous $NaHCO_3$ and brine then dried over $MgSO_4$. Evaporation of the solvent under reduced pressure gave a residue which was chromatographed on silica gel. Elution with mixtures of ethyl acetate/hexane provided the title compound (192 mg), containing an equimolar quantity of the isomeric cepham, as an amorphous white solid; $\nu_{max}$ ($CH_2Cl_2$) 3397, 3330, 1772 and 1738 cm$^{-1}$.

PREPARATION 9

Benzyl 2β-(3,4-diacetoxybenzoyloxy)methyl-6β-[R,2-(4-ethyl-2,3-dioxopiperazin-1-yl)carbonylamino-2-phenylacetamido]-2α-methylpenam-3-carboxylate Benzyl 6β-amino-2β-(3,4-diacetoxybenzoyloxy)methyl-2α-methylpenam-3-carboxylate (190 mg, the product from Preparation C containing an equimolar quantity of the isomeric cepham) was dissolved in dry $CH_2Cl_2$ (5 ml) and a solution of R,2-[(4-ethyl-2,3-dioxopiperazin-1-yl)carbonylamino]-2-phenylacetyl chloride (prepared from the corresponding acid (319 mg, 1.0 mmol) as described in Preparation 5(a)) in dry CH$_2$Cl$_2$ (5 ml) was added. Pyridine (79 mg, 1.0 mmol) was added and the mixture stirred for 2 h; EtOAc was then added and the solution washed with 0.1M aqueous HCl, saturated aqueous NaHCO$_3$ and brine then dried over MgSO$_4$. Evaporation of the solvent under reduced pressure provided a solid residue which was chromatographed on silica gel. Elution with EtOAc/hexane and MeOH/EtOAc mixture provided pure title compound (44 mg); $\nu_{max}$ (CH$_2$Cl$_2$) 3320, 1775, 1745, 1715 and 1690 cm$^{-1}$; $\delta_H$ (CD$_3$COCD$_3$) 10.0 (1H, d, 7.2 Hz), 8.24 (1H, d, 8.4 Hz), 7.86 (2H, m), 7.40 (11H, m), 5.68 (3H, m), 5.28 (2H, s), 4.93 (1H, s), 4.36 (1H, d, 11.5 Hz), 4.19 (1H, d, 11.5 Hz), 4.04 (2H, m), 3.69 (2H, m), 3.50 (2H, q, 7.2 Hz), 2.33 (3H, s), 2.32 (3H, s), 1.49 (3H, s), 1.16 (3H, t, 7.2 Hz); [F.A.B. (Thioglycerol) (+ve ion) MH+844].

EXAMPLE 3

Sodium 2β-(3,4-diacetoxybenzoyloxy)methyl-6β-[R,2-(4-ethyl-2,3-dioxopiperazin-1-yl)carbonylamino-2-phenylacetamido]-2α-methylpenam-3-carboxylate Benzyl 2β-(3,4-diacetoxybenzoyloxy)methyl-[R,2-(4-ethyl-2,3-dioxopiperazin-1-yl)carbonylamino-2-phenylacetamido]-2α-methylpenam-3-carboxylate (35 mg, 0.0415 mmol) was dissolved in dry THF (7 ml) and the solution added to the 10% Pd-charcoal catalyst (35 mg). The mixture was hydrogenated at ambient temperature and pressure for 2 hours. After filtration through a Kieselguhr plug the filtrate was evaporated under reduced pressure. The residue was suspended in distilled water (20 ml) and the pH carefully adjusted to 6.8 using dilute aqueous NaHCO$_3$. The solution was filtered and the filtrate lyophilised to give the title compound (27 mg); $\nu$hd max (KBr) 1771, 1714, 1683 and 1613 cm$^{-1}$; $\delta_H$(D$_2$O) 7.96 (1H, dd, 8.5 and 1.9 Hz), 7.87 (1H, d, 1.9 Hz), 7.43–7.15 (6H, m), 5.55 (1H, d, 3.7 Hz), 5.4 (2H, m), 4.52 (1H, s), 4.22 (2H, ABq), 3.90 (2H, m), 3.60 (2H, m), 3.45 (2H, m), 2.35 (6H, 2s), 1.52 (3H, s), 1.15 (3H, m); [F.A.B. (Thioglycerol) (+ve ion) MH+776].

EXAMPLE 4

Sodium 6β-[R,2-(4-ethyl-2,3-dioxopiperazin-1-yl) carbonylamino-2-phenylacetamido]-2β-(3,4-dihydroxybenzoyloxy)methyl-2α-methylpenam-3-carboxylate A solution of sodium 2β-(3,4-diacetoxybenzoyloxy) methyl-6β-[R,2-(4-ethyl-2,3-dioxopiperazin-1-yl) carbonylamino-2-phenylacetamido]-2α-methylpenam-3-carboxylate (15 mg, 0.019 mmol) in 0.05M aqueous KH$_2$PO$_4$ (4 ml) was treated with a citrus acetyl esterase preparation (ex. Sigma) (0.2 ml, equivalent to approx. 0.8 mg protein). The pH was adjusted to 7.0 with 0.05M aqueous NaOH. The reaction was monitored by reverse phase HPLC. After 40 minutes the reaction mixture was chromatographed on HP20SS resin, eluting first with water, then with acetone/water mixtures. The product containing eluant was concentrated under reduced pressure, then lyophilised to give the title compound (7.2 mg); $\nu_{max}$ (KBr) 1773, 1710, 1684 and 1609 cm$^{-1}$; $\delta_H$ (D$_2$O) 7.52–7.10 (7H, m), 6.93 (1H, d, 8.2 Hz), 5.55 (1H, d, 3.8 Hz), 5.41 (1H, d, 3.8 Hz), 5.32 (1H, s), 4.21 (2H, ABq), 3.9 (2H, m), 3.6 (2H, m), 3.43 (2H, q, 7.3 Hz), 1.52 (3H, s), 1.15 (3H, t, 7.3 Hz).

EXAMPLE 5

Minimum Inhibitory concentration (MIC) values of compounds of the invention against *E. coli* JT425 and DC RTEM, *K. Pneumoniae* T767 and *P. aeruginosa* 10662 and K79961. were determined by serial dilution in Iso-sensitest Agar (from Oxoid Ltd., Basingstoke, England). The plates were inoculated with 10$^4$ colony forming units and incubated overnight at 37° C. The MIC values recorded in Table 1 were the lowest concentration of antibiotic to inhibit growth. Comparative data for Piperacillin which is the compound 6β-[D-2-[(4-ethyl-2,3-dioxopiperazin-1-yl)carbonylamino]-2-phenylacetamido]-penicillanic acid, sodium salt and for the compound 6α-formamido-6β-[D-2-[(4-ethyl-2,3-dioxopiperazin-1-yl)carbonylamino]-2-phenylacetamido]-penicillanic acid, sodium salt (Compound A) disclosed in U.K. GB Pat. No.-2107307B, are also given.

TABLE 1

| | MIC data | | | | |
|---|---|---|---|---|---|
| | MIC (μg/ml) | | | | |
| Organism | Example 1 | Example 2 | Example 3 | Piperacillin | Compound A |
| *E. coli* JT 425 | 0.5 | 0.5 | 1.0 | 16 | 8.0 |
| *E. coli* DC RTEM | 0.12 | <0.03 | 4.0 | >128 | 4.0 |
| *K. pneumoniae* T767 | 0.12 | 0.12 | 0.25 | 2.0 | 4.0 |
| *P. aeruginosa* 10662 | 0.25 | 0.12 | <0.03 | 2.0 | 16 |
| *P. aeruginosa* K79961 | 0.06 | <0.03 | <0.03 | >0.06 | 2.0 |

We claim:

1. A compound of the formula:

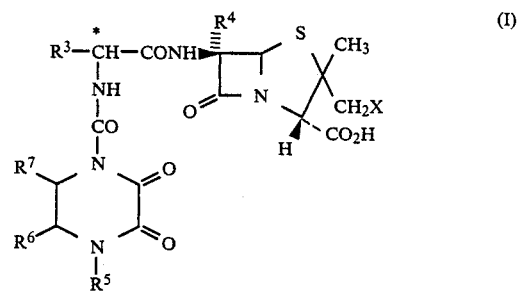

a pharmaceutically acceptable salt or in vivo hydrolyzable ester thereof wherein R$^3$ is phenyl, unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms, oxoalkyl of 1 to 6 carbon atoms, alkylcarbonyl of 1 to 6 carbon atoms in the alkyl moiety, aryloxy, aralkyloxy, arylcarbonyl, alkylamino of 1 to 6 carbon atoms in the alkyl moiety, di-alkylamino of 1 to 6 carbon atoms in each alkyl moiety and protected amino, cyclohexenyl, cyclohexadienyl or a 5- or 6-membered heterocyclic ring containing up to three heteroatoms selected from the group consisting of oxygen, sulphur and nitrogen unsubstituted or substituted by hydroxy, amino, halo or alkoxy of 1 to 6 carbon atoms, and wherein aryl is phenyl or naphthyl unsubstituted or substituted with up to five substituents selected from the group consisting of halo, alkyl of 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety; $R^4$ is hydrogen or formamido; $R^5$ is hydrogen, alkyl of 1 to 6 carbon atoms, aryl or aralkyl wherein aryl is as above defined and alkyl is of 1 to 6 carbon atoms; $R^6$ and $R^7$ are the same or different and each is hydrogen, alkyl of 1 to 6 carbon atoms, halo, amino, phenyl unsubstituted or substituted with up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms, oxoalkyl of 1 to 6 carbon atoms, alkylcarbonyl of 1 to 6 carbon atoms in the alkyl moiety, aryloxy, aralkyloxy, arylcarbonyl, alkylamino of 1 to 6 carbon atoms in the alkyl moiety, dialkylamino of 1 to 6 carbon atoms in each alkyl moiety and protected amino, hydroxy or alkoxy of 1 to 6 carbon atoms, or $R^6$ and $R^7$ form the residue of a 5- or 6-membered carbocyclic ring or a 5- or 6-membered heterocyclic ring containing up to three hetero atoms selected from the group consisting of oxygen, sulphur and nitrogen unsubstituted or substituted by hydroxy, amino, halo, or alkoxy of 1 to 6 carbon atoms; and X is

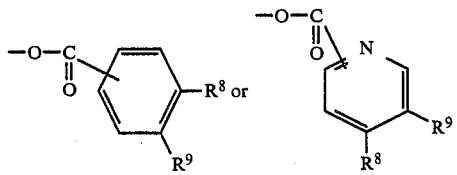

or tautomers thereof wherein $R^8$ and $R^9$ are the same or different and each is hydroxy, or protected hydroxy.

2. A pharmaceutical composition useful for treating bacterial infections in humans and animals which comprises an antibacterially effective amount of a compound of the formula

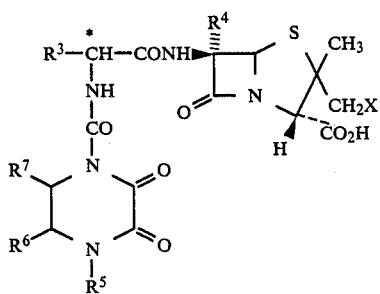

(I)

a pharmaceutically acceptable salt or in vivo hydroly ester thereof wherein $R^3$ is phenyl, unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms, oxoalkyl of 1 to 6 carbon atoms, alkylcarbonyl of 1 to 6 carbon atoms in the alkyl moiety, aryloxy, aralkyloxy, arylcarbonyl, alkylamino of 1 to 6 carbon atoms in the alkyl moiety, di-alkylamino of 1 to 6 carbon atoms in each alkyl moiety and protected amino, cyclohexenyl, cyclohexadienyl or a 5- or 6-membered heterocyclic ring containing up to three heteroatoms selected from the group consisting of oxygen, sulphur and nitrogen unsubstituted or substituted by hydroxy, amino, halo or alkoxy of 1 to 6 carbon atoms, and wherein aryl is phenyl or naphthyl unsubstituted or substituted with up to five substituents selected from the group consisting of halo, alkyl of 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety; $R^4$ is hydrogen or formamido; $R^5$ is hydrogen, alkyl of 1 to 6 carbon atoms, aryl or aralkyl wherein aryl is as above defined and alkyl is of 1 to 6 carbon atoms; $R^6$ and $R^7$ are the same or different and each is hydrogen, alkyl of 1 to 6 carbon atoms, halo, amino, phenyl unsubstituted or substituted with up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms, oxoalkyl of 1 to 6 carbon atoms, alkylcarbonyl of 1 to 6 carbon atoms in the alkyl moiety, aryloxy, aralkyloxy, arylcarbonyl, alkylamino of 1 to 6 carbon atoms in the alkyl moiety, di-alkylamino of 1 to 6 carbon atoms in each alkyl moiety and protected amino, hydroxy or alkoxy of 1 to 6 carbon atoms, or $R^6$ and $R^7$ form the residue of a 5- or 6-membered carbocyclic ring or a 5- or 6-membered heterocyclic ring containing up to three hetero atoms selected from the group consisting of oxygen, sulphur and nitrogen unsubstituted or substituted by hydroxy, amino, halo, or alkoxy of 1 to 6 carbon atoms; and X is

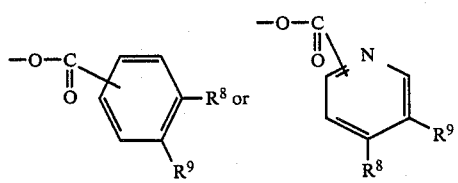

or tautomers thereof wherein $R^8$ and $R^9$ are the same or different and each is hydroxy, or protected hydroxy, in combination with a pharmaceutically acceptable carrier.

3. A composition according to claim 2 in which $R^3$ is phenyl or 4-hydroxyphenyl.

4. A composition according to claim 2 in which $R^4$ is formamido.

5. A composition according to claim 2 in which $R^6$ and $R^7$ are both hydrogen.

6. A composition according to claim 2 in which $R^5$ is ethyl.

7. A composition according to claim 2 wherein the compound is selected from the group consisting of the following and pharmaceutically acceptable salts and pharmaceutically acceptable in vivo hydrolyzable esters thereof:

2β-(3,4-Diacetoxybenzoyloxy)methyl-6β-[R,2-(4-ethyl-2,3-dioxopiperazin-1-yl)carbonylamino-2-phenyl acetamido]-6α-formamido-2α-methylpenam-3-carboxylic acid;

6β-[R2-(4-Ethyl-2,3-dioxopiperazin-1-yl)carbonyl amino-2-phenylacetamido]-6α-formamido-2β-(3,4-dihydroxy benzoyloxy)methyl-2α-methylpenam-3-carboxylic acid;

2β-(3,4-Diacetoxybenzoyloxy)methyl-6β-[R,2-(4-ethyl-2,3-dioxopiperazin-1-yl)carbonylamino-2-phenylacetamido]-2α-methylpenam-3-carboxylic acid; and 6β-[R,2-(4-Ethyl-2,3-dioxopiperazin-1-yl)carbonylamino-2-phenylacetamido]-2β-(3,4-dihydroxybenzoyloxy) methyl-2α-methylpenam-3-carboxylic acid.

8. A method of treating bacterial infections in humans and animals which comprises administering to a human or animal in need thereof an antibacterially effective amount of a compound of the formula

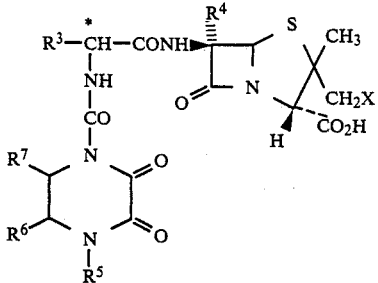

(I)

a pharmaceutically acceptable salt or in vivo hydroly ester thereof wherein $R^3$ is phenyl, unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms, oxoalkyl of 1 to 6 carbon atoms, alkylcarbonyl of 1 to 6 carbon atoms in the alkyl moiety, aryloxy, aralkyloxy, arylcarbonyl, alkylamino of 1 to 6 carbon atoms in the alkyl moiety, di-alkylamino of 1 to 6 carbon atoms in each alkyl moiety and protected amino, cyclohexenyl, cyclohexadienyl or a 5- or 6-membered heterocyclic ring containing up to three heteroatoms selected from the group consisting of oxygen, sulphur and nitrogen unsubstituted or substituted by hydroxy, amino, halo or alkoxy of 1 to 6 carbon atoms, and wherein aryl is phenyl or naphthyl unsubstituted or substituted with up to five substituents selected from the group consisting of halo, alkyl or 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety; $R^4$ is hydrogen or formamido; $R^5$ is hydrogen, alkyl of 1 to 6 carbon atoms, aryl or aralkyl wherein aryl is as above defined and alkyl is of 1 to 6 carbon atoms; $R^6$ and $R^7$ are the same or different and each is hydrogen, alkyl of 1 to 6 carbon atoms, halo, amino, phenyl unsubstituted with up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms, oxoalkyl of 1 to 6 carbon atoms, alkylcarbonyl of 1 to 6 carbon atoms in the alkyl moiety, aryloxy, aralkyloxy, arylcarbonyl, alkylamino of 1 to 6 carbon atoms in the alkyl moiety, di-alkylamino of 1 to 6 carbon atoms in each alkyl moiety and protected amino, hydroxy or alkoxy of 1 to 6 carbon atoms, or $R^6$ and $R^7$ form the residue of a 5- or 6-membered carbocyclic ring or a 5- or 6-membered heterocyclic ring containing up to three hetero atoms selected from the group consisting of oxygen, sulphur and nitrogen unsubstituted or substitued by hydroxy, amino, halo, or alkoxy of 1 to 6 carbon atoms; and X is

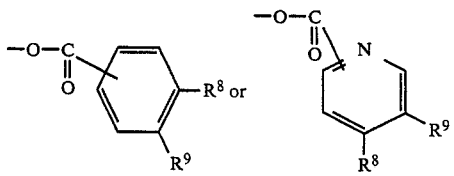

or tautomers thereof wherein $R^8$ and $R^9$ are the same or different and each is hydroxy, or protected hydroxy, in combination with a pharmaceutically acceptable carrier.

9. A method according to claim 8 in which $R^3$ is phenyl or 4-hydroxyphenyl.

10. A method according to claim 8 in which $R^4$ is formamido.

11. A method according to claim 8 in which $R^6$ and $R^7$ are both hydrogen.

12. A method according to claim 8 in which $R^5$ is ethyl.

13. A method according to claim 8 wherein the compound is selected from the group consisting of the following and pharmaceutically acceptable salts and pharmaceutically acceptable in vivo hydrolyzable esters thereof:

2β-(3,4-Diacetoxybenzoyloxy)methyl-6β-[R,2-(4-ethyl-2,3-dioxopiperazin-1-yl)carbonylamino-2-phenyl acetamido]-6α-formamido-2α-methylpenam-3-carboxylic acid;

6β-[R,2-(4-Ethyl-2,3-dioxopiperazin-1-yl)carbonyl amino-2-phenylacetamido]-6α-formamido-2β-(3,4-dihydroxy benzoyloxy)methyl-2α-methylpenam-3-carboxylic acid;

2β-(3,4-Diacetoxybenzoyloxy)methyl-6β-[R,2-(4-ethyl-2,3-dioxopiperazin-1-yl)carbonylamino-2-phenylacetamido]-2α-methylpenam-3-carboxylic acid; and 6β-[R,2-(4-Ethyl-2,3-dioxopiperazin-1-yl)carbonylamino-2-phenylacetamido]-2β-(3,4-dihydroxybenzoyloxy) methyl-2α-methylpenam-3-carboxylic acid.

14. A pharmaceutical composition useful for treating bacterial infections in humans and animals which comprises an antibacterially effective amount of a compound of the formula

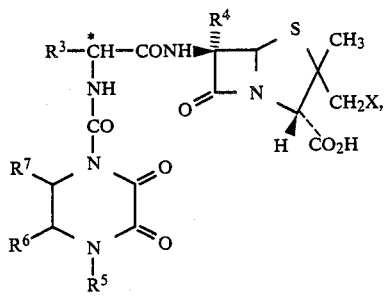

a pharmaceutically acceptable salt or in vivo hydroly ester thereof wherein $R^3$ is phenyl, unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms, oxoalkyl of 1 to 6 carbon atoms, alkylcarbonyl of 1 to 6 carbon atoms in the alkyl moiety, aryloxy, aralkyloxy, arylcarbonyl, alkylamino of 1 to 6 carbon atoms in the alkyl moiety, di-alkylamino of 1 to 6 carbon atoms in each alkyl moiety and protected amino, cyclohexenyl, cyclohexadienyl or a 5- or 6-membered heterocyclic ring containing up to three heteroatoms selected from the group consisting of oxygen, sulphur and nitrogen unsubstituted or substituted by hydroxy, amino, halo or alkoxy of 1 to 6 carbon atoms, and wherein aryl is phenyl or naphthyl unsubstituted or substituted with up to five substituents selected from the group consisting of halo, alkyl of 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety; $R^4$ is hydrogen or formamido; $R^5$ is hydrogen, alkyl of 1 to 6 carbon atoms, aryl or aralkyl wherein aryl is as above defined and alkyl is of 1 to 6 carbon atoms; $R^6$ and $R^7$ are the same or different and each is hydrogen, alkyl of 1 to 6 carbon atoms, halo, amino, phenyl unsubstituted or substituted with up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms, oxoalkyl of 1 to 6 carbon atoms, alkylcarbonyl of 1 to 6 carbon atoms in the alkyl moiety, aryloxy, aralkyloxy, arylcarbonyl, alkylamino of 1 to 6 carbon atoms in the alkyl moiety, di-alkylamino of 1 to 6 carbon atoms in each alkyl moiety and protected amino, hydroxy or alkoxy of 1 to 6 carbon atoms, or $R^6$ and $R^7$ form the residue of a 5- or 6-membered carbocyclic ring or a 5- or 6-membered heterocyclic ring containing up to three hetero atoms selected from the group consisting of oxygen, sulphur and nitrogen unsubstituted or substituted by hydroxy, amino, halo, or alkoxy of 1 to 6 carbon atoms; and X is

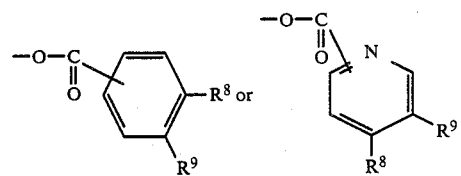

or tautomers thereof wherein $R^8$ and $R^9$ are the same or different and each is hydroxy, or protected hydroxy, and a β-lactamase inhibitory amount of a β-lactamase inhibitor, in combination with a pharmaceutically acceptable carrier.

15. A composition according to claim 14 in which $R^3$ is phenyl or 4-hydroxyphenyl.

16. A composition according to claim 14 in which $R^4$ is formamido.

17. A composition according to claim 14 in which $R^6$ and $R^7$ are both hydrogen.

18. A composition according to claim 14 in which $R^5$ is ethyl.

19. A composition according to claim 14 wherein the compound is selected from the group consisting of the following and pharmaceutically acceptable salts and pharmaceutically acceptable in vivo hydrolyzable esters thereof:

2β-(3,4-Diacetoxybenzoyloxy)methyl-6β-[R,2-(4-ethyl-2,3-dioxopiperazin-1-yl)carbonylamino-2-phenyl acetamido]-6α-formamido-2α-methylpenam-3-carboxylic acid;

6β-[R,2-(4-Ethyl-2,3-dioxopiperazin-1-yl)carbonyl amino-2-phenylacetamido]-6α-formamido-2β-(3,4-dihydroxy benzoyloxy)methyl-2α-methylpenam-3-carboxylic acid;

2β-(3,4-Diacetoxybenzoyloxy)methyl-6β-[R,2-(4-ethyl-2,3-dioxopiperazin-1-yl)carbonylamino-2-phenylacetamido]-2α-methylpenam-3-carboxylic acid; and 6β-[R,2-(4-Ethyl-2,3-dioxopiperazin-1-yl)carbonylamino-2-phenylacetamido]-2β-(3,4-dihydroxybenzoyloxy) methyl-2α-methylpenam-3-carboxylic acid.

20. A method of treating bacterial infections in humans and animals which comprises administering to a human or animal in need thereof an antibacterially effective amount of a compound of the formula

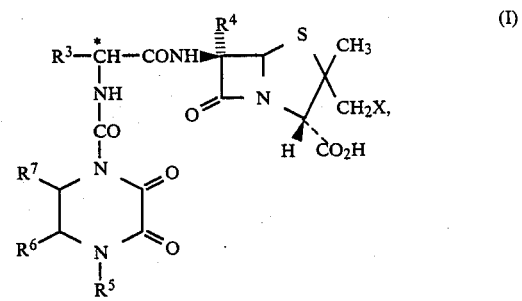

a pharmaceutically acceptable salt or in vivo hydroly ester thereof wherein $R^3$ is phenyl, unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms, oxoalkyl of 1 to 6 carbon atoms, alkylcarbonyl of 1 to 6 carbon atoms in the alkyl moiety, aryloxy, aralkyloxy, arylcarbonyl, alkylamino of 1 to 6 carbon atoms in the alkyl moiety, di-alkylamino of 1 to 6 carbon atoms in each alkyl moiety and protected amino, cyclohexenyl, cyclohexadienyl or a 5- or 6-membered heterocyclic ring containing up to three heteroatoms selected from the group consisting of oxygen, sulphur and nitrogen unsubstituted or substituted by hydroxy, amino, halo or alkoxy of 1 to 6 carbon atoms, and wherein aryl is phenyl or naphthyl unsubstituted or substituted with up to five substituents selected from the group consisting of halo, alkyl of 1 to 6 carbon atoms, phenyl, alkoxy of 1 to 6 carbon atoms, haloalkyl of 1 to 6 carbon atoms, hydroxy, amino, nitro, carboxy, alkoxycarbonyl of 1 to 6 carbon atoms, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety; $R^4$ is hydrogen or formamido; $R^5$ is hydrogen, alkyl of 1 to 6 carbon atoms, aryl or aralkyl wherein aryl is as above defined an alkyl of 1 to 6 carbon atoms; $R^6$ and $R^7$ are the same or different and each is hydrogen, alkyl of 1 to 6 carbon atoms, halo, amino, phenyl unsubstituted or substituted with up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms in the alkyl moiety, carboxy, alkoxycarbonyl of 1 to 6 carbon atoms in the alkoxy moiety, haloalkyl of 1 to 6 carbon atoms, oxoalkyl of 1 to 6 carbon atoms, alkylcarbonyl of 1 to 6 carbon atoms in the alkyl moiety, aryloxy, aralkyloxy, arylcarbonyl, alkylamino of 1 to 6 carbon atoms in the alkyl moiety, di-alkylamino of 1 to 6 carbon atoms in each alkyl moiety and protected amino, hydroxy or alkoxy of 1 to 6 carbon atoms, or $R^6$ and $R^7$ form the residue of a 5- or 6-membered carbocyclic ring or a 5- or 6-membered heterocyclic ring containing up to three hetero atoms selected from the group consisting of oxygen, sulphur and nitrogen unsubstituted or substituted by hydroxy, amino, halo, or alkoxy of 1 to 6 carbon atoms; and X is

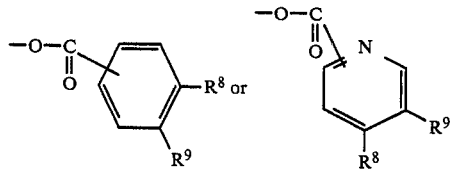

or tautomers thereof wherein $R^8$ and $R^9$ are the same or different and each is hydroxy, or protected hydroxy, and a β-lactamase inhibitory amount of a β-lactamase inhibitor, in combination with a pharmaceutically acceptable carrier.

21. A method according to claim 20 in which $R^3$ is phenyl or 4-hydroxyphenyl.

22. A method according to claim 20 in which $R^4$ is formamido.

23. A method according to claim 20 in which $R^6$ and $R^7$ are both hydrogen.

24. A method according to claim 20 in which $R^5$ is ethyl.

25. A method according to claim 20 wherein the compound is selected from the group consisting of the following and pharmaceutically acceptable salts and pharmaceutically acceptable in vivo hydrolyzable esters thereof:

2β-(3,4-Diacetoxybenzoyloxy)methyl-6β-[R,2-(4-ethyl-2,3-dioxopiperazin-1-yl)carbonylamino-2-phenyl acetamido]-6α-formamido-2α-methylpenam-3-carboxylic acid;

6β-[R,2-(4-Ethyl-2,3-dioxopiperazin-1-yl)carbonyl amino-2-phenylacetamido]-6α-formamido-2β-(3,4-dihydroxy benzoyloxy)methyl-2α-methylpenam-3-carboxylic acid;

2β-(3,4-Diacetoxybenzoyloxy)methyl-6β-[R,2-(4-ethyl-2,3-dioxopiperazin-1-yl)carbonylamino-2-phenylacetamido]-2α-methylpenam-3-carboxylic acid; and 6β-[R,2-(4-Ethyl-2,3-dioxopiperazin-1-yl)carbonylamino-2-phenylacetamido]-2β-(3,4-dihydroxybenzoyloxy) methyl-2α-methylpenam-3-carboxylic acid.

26. A compound according to claim 1 in which $R^3$ is phenyl or 4-hydroxyphenyl.

27. A compound according to claim 1 in which $R^4$ is formamido.

28. A compound according to claim 1 in which $R^6$ and $R^7$ are both hydrogen.

29. A compound according to claim 1 in which $R^5$ is ethyl.

30. A compound according to claim 1 selected from the group consisting of the following and pharmaceutically acceptable salts and pharmaceutically acceptable in vivo hydrolysable esters thereof:

2β-(3,4-Diacetoxybenzoyloxy)methyl-6β-[R,2-(4-ethyl-2,3-dioxopiperazin-1-yl)carbonylamino-2-phenyl acetamido]-6α-formamido-2α-methylpenam-3-carboxylic acid;

6β-[R,2-(4-Ethyl-2,3-dioxopiperazin-1-yl)carbonyl amino-2-phenylacetamido]-6α-formamido-2β-(3,4-dihydroxy benzoyloxy)methyl-2α-methylpenam-3-carboxylic acid;

2β-(3,4-Diacetoxybenzoyloxy)methyl-6β-[R,2-(4-ethyl-2,3-dioxopiperazin-1-yl)carbonylamino-2-phenylacetamido]-2α-methylpenam-3-carboxylic acid; and 6β-[R,2-(4-Ethyl-2,3-dioxopiperazin-1-yl)carbonylamino-2-phenylacetamido]-2β-(3,4-dihydroxybenzoyloxy) methyl-2α-methylpenam-3-carboxylic acid.

* * * * *

UNITED STATES PATENT AND TRADEMARK OFFICE
CERTIFICATE OF CORRECTION

PATENT NO. : 4,820,701
DATED     : April 11, 1989
INVENTOR(S) : Robert Southgate and Colin H. Frydrych It is certified that error appears in the above-identified patent and that said Letters Patent is hereby corrected as shown below:

On the face of the patent document, please insert

--Foreign Priority Application Data

April 23, 1987 [GB]  United Kingdom...8709666--

Signed and Sealed this

Sixth Day of February, 1990

*Attest:*

JEFFREY M. SAMUELS

*Attesting Officer*    *Acting Commissioner of Patents and Trademarks*